United States Patent
Klappenberger

[11] Patent Number: 5,967,143
[45] Date of Patent: Oct. 19, 1999

[54] SURGICAL INSTRUMENT FOR EMERGENCY MEDICINE

[76] Inventor: Jurgen Klappenberger, Bannhofstr. 11, 94327 Bogen, Germany

[21] Appl. No.: 09/141,234

[22] Filed: Aug. 27, 1998

[30] Foreign Application Priority Data

Sep. 2, 1997 [DE] Germany .................... 197 38 539

[51] Int. Cl.$^6$ .................................... A61M 16/00
[52] U.S. Cl. ................. 128/207.29; 128/200.56; 128/205.13
[58] Field of Search ............ 128/200.24, 200.26, 128/205.13, 205.17, 207.29

[56] References Cited

U.S. PATENT DOCUMENTS

| | | | |
|---|---|---|---|
| 1,177,208 | 3/1916 | Pierpont | 128/202.28 |
| 2,923,299 | 2/1960 | Blackwood . | |
| 2,970,749 | 2/1961 | Montague | 128/205.13 |
| 3,476,112 | 11/1969 | Elstein . | |
| 3,476,113 | 11/1969 | Tarsitano | 128/207.29 |
| 3,893,454 | 7/1975 | Hagelin . | |
| 3,906,956 | 9/1975 | Gilbert | 128/207.29 |
| 3,916,903 | 11/1975 | Pozzi | 128/207.29 |
| 3,991,765 | 11/1976 | Cohen | 128/207.29 |
| 4,003,381 | 1/1977 | Gilbert | 128/207.29 |
| 4,539,985 | 9/1985 | Magrath | 128/205.13 |
| 4,593,687 | 6/1986 | Gray et al. | 128/200.26 |
| 4,791,690 | 12/1988 | Kuang-Wu | 7/138 |
| 4,898,163 | 2/1990 | George | 128/200.26 |
| 5,245,991 | 9/1993 | Kawaguchi | 128/200.24 |
| 5,507,279 | 4/1996 | Fortune et al. | 128/200.26 |
| 5,546,939 | 8/1996 | French | 128/207.29 |
| 5,569,300 | 10/1996 | Redman | 606/207 |

FOREIGN PATENT DOCUMENTS

WO91/07202  5/1991  WIPO ............... 128/207.29

Primary Examiner—Aaron J. Lewis
Attorney, Agent, or Firm—Kane, Dalsimer, Sullivan, Kurucz, Levy, Eisele and Richard, LLP

[57] ABSTRACT

The invention relates to a surgical instrument, especially for emergency medicine, in particular a so-called coniotomy device with which access to the lung is created for supplying air to the lung in cases in which breathing is hindered in the larynx, which device can be fixated internally and externally and has a short, straight indwelling cannula with a fixative rim at its end and with a trocar, the cutting edge of which is perpendicular to the cricoid cartilage, does not allow any wall contacts within the trachea, causes no injuries to the elastic fibers of the ligamentum conicum and can also be equipped with a small closure sac inserted into the trachea along with the cannula, which can be blown up from outside and which makes it possible to close the trachea in the upwards direction, preventing any escape from the trachea of the breathing air blown into the indwelling cannula.

9 Claims, 2 Drawing Sheets

SURGICAL INSTRUMENT FOR EMERGENCY MEDICINE

BACKGROUND OF THE INVENTION

1. Field of the Invention

The invention relates to a surgical instrument for emergency medicine, in particular a so-called coniotomy device with a trocar, an indwelling cannula that can be inserted into the trachea and a collar affixed outside to the neck.

2. Description of Related Art

Coniotomy devices of this type are known to the art. The German Patent 88 85 715 C7, for instance, describes such a device, under which a collar to be positioned on the neck, with a flange inclined at an angle of less than 45 degrees to the collar surface, is equipped with a fastening component, into which an axially conducted catheter system with a cannula and stylet can be inserted and, after the successful introduction into the breathing tract, can be arrested by means of a clamp stop on the fastening component.

Moreover, U.S. Pat. No. 3,906,956 describes such an instrument that has an L-shaped configuration and an opening for a trocar.

Furthermore, U.S. Pat. No. 4,791,690 discloses a similar instrument that features a self-limiting depth penetration device, restricting penetration to the back third of the trachea, and has tube-shaped nozzles originating on both sides from an oval flange, allowing passage of an air tube to be inserted into the trachea.

Finally, similar instruments have become known from the two U.S. Pat. Nos. 3,476,112 and 2,923,299 and the German Patent 19 514 433.

It is evident that these known coniotomy devices have considerable disadvantages. Their structure is too complicated for use in emergencies, consisting as they do of too many individual parts to be assembled prior to use. Moreover, they are too difficult to manipulate even for an experienced physician in such situations, leading to the loss of valuable time that could possibly be decisive in saving the life of the patient. Instruments equipped with complicated mechanics and with cannulas inserted into the trachea in bent form can rarely be used in real-life situations; in particular, those with bent cannulas are totally inappropriate for emergency medicine.

SUMMARY OF THE INVENTION

This is where the invention can help. The object of the invention, as described in the claims, is to create a coniotomy device that is simple in structure, fast and easy to manipulate, one that allows for visual inspection of the trachea and, if needed, i.e., in the case of severe injuries, for instance in the area of the jaw, one that securely prevents the escape through the upper section of the larynx of air introduced into the trachea.

The advantages associated with the invention include in particular its simple structure, being a coniotomy device that consists of only two self-fixating parts, assuring both internal and external fixation by means of the circular rim at the end of the indwelling cannula and the lateral fixative wings of the base section, as well as its quick and easy handling, thanks to its straight form, an extremely important advantage especially in severe emergencies. Furthermore, the device does not allow for any contact of the instrument with the inner wall of the trachea, which largely rules out the danger of reflexive spasms. A further advantage lies in the fact that the cutting edge, thanks to its perpendicular alignment, prevents the transection of the elastic fibers of the lig. conicum, thereby making later, otherwise unavoidable plastic surgery unnecessary. Moreover, the ability to inspect visually the trachea, made possible by the short, straight form of the indwelling cannula, represents a significant advantage. Moreover, thanks to the possibility of inserting a small closure sac into the trachea, the upwards escape of air blown into the trachea can be prevented. Finally, the insertion of the blocking cannula into the base section is totally unproblematic.

BRIEF DESCRIPTION OF THE DRAWINGS

In the following, the invention is described in more detail with the aid of the execution examples depicted in the figures, wherein.

DESCRIPTION OF THE PREFERRED EMBODIMENTS

Figure 1A:
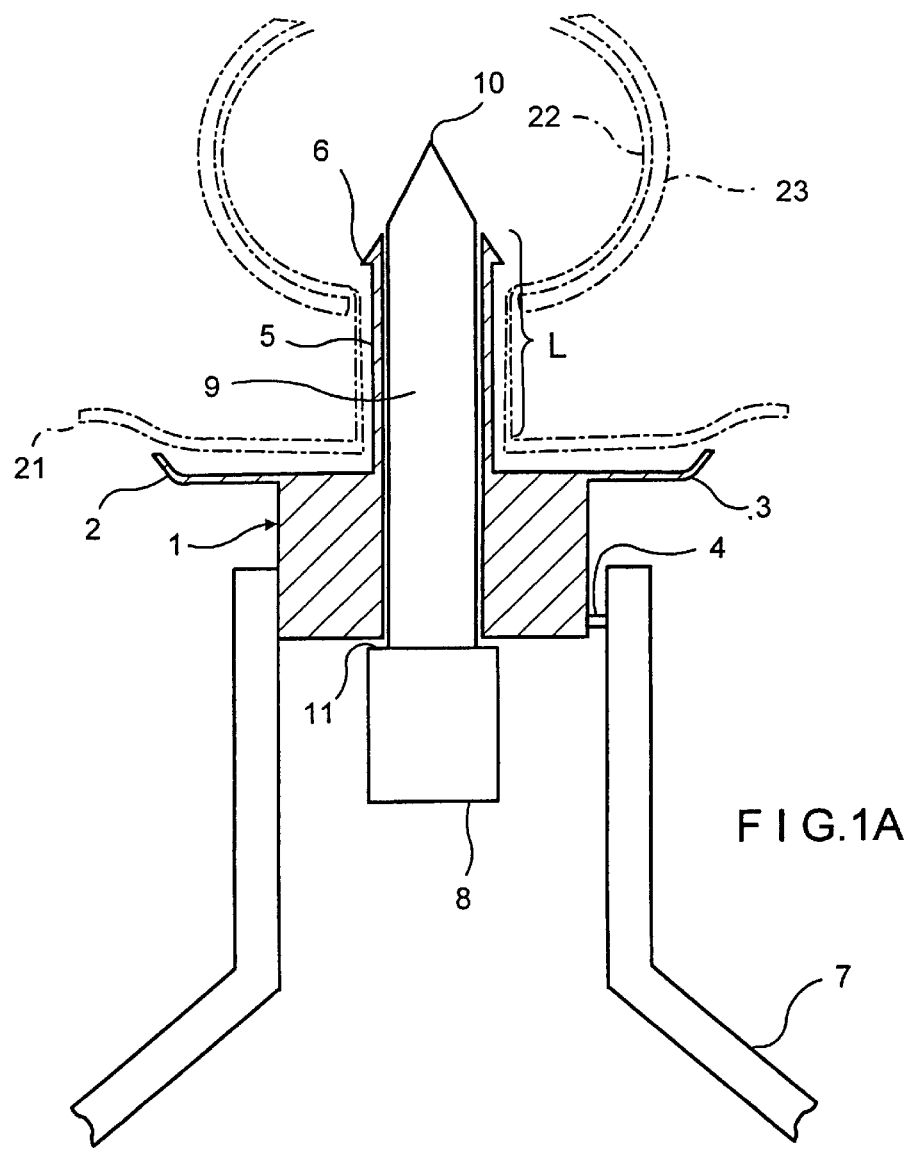
FIG. 1 shows a horizontal section through the coniotomy device with trocar.
Figure 1B:
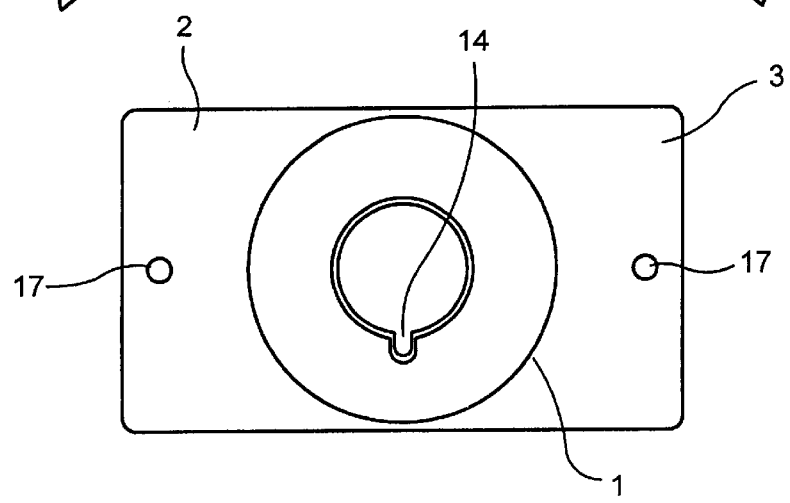
Figure 2A:
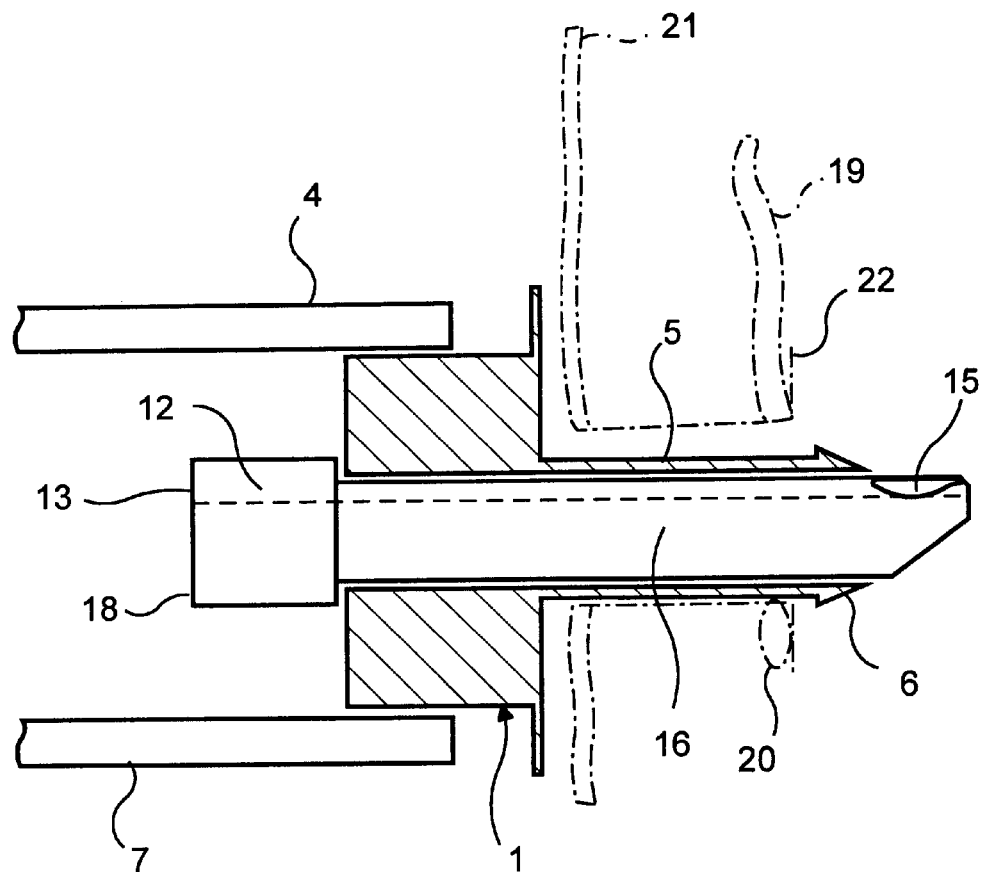
FIG. 2 shows a vertical section of FIG. 1 with a blocking cannula, both in top view.
Figure 2B:
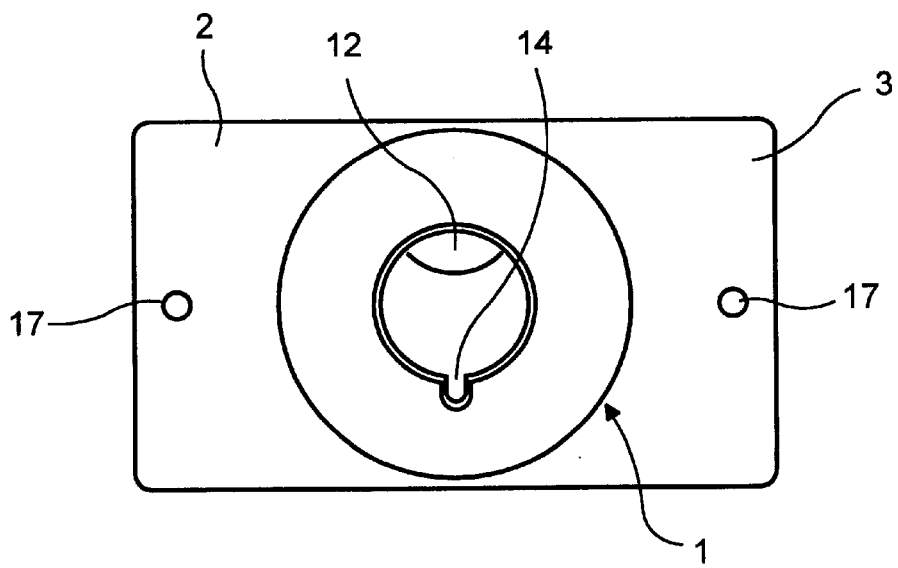

As can be seen in FIG. 1, the coniotomy device consists essentially of only two parts, namely the base section 1 and the trocar 8. The base section 1 is equipped with two fixative wings 2 and 3, with which it is affixed externally to the patient=s neck. The number 17 designates an eyelet in each case. Furthermore, the base section 1 has an attachment 4 for the so-called ambulatory bag, only suggested in the figure, as well as an air-pump squeeze-pouch 7 and an indwelling cannula to be inserted into the trachea 23 of the patient. The indwelling cannula 5 is short and has a circular fixative rim 6 at the end, which prevents the coniotomy device from slipping out once it has been introduced into the trachea 23. Consequently, the device is affixed both externally and internally. The trocar 8 has a scalpel-like cutting edge 10 with a perpendicular alignment and, in certain cases, a limit stop 11 with which the penetration depth of the trocar 8 can be restricted.

To facilitate understanding, the thyroid cartilage is designated with 19, the cricoid cartilage with 20, the skin with 21 and the mucus membrane of the trachea 23 with the number 22 in the figures.

It has proven advantageous to limit the optimal length L of the indwelling cannula 5 between the base section 1 and its end to about 17 mm, including the rim at the end, which should be about 1 mm thick. For special applications, the indwelling cannula 5 can have a telescopic design, for instance, so that its length can be adjusted as needed. The inner diameter of the indwelling cannula 5 is adequately dimensioned with 4–6 mm, 6 mm being provided as the diameter for large-sized adults. To prevent the trocar 8 from twisting, a fixative groove and tongue device 14 is also provided at least in a partial section of the indwelling cannula 5 and the trocar 8 or its shaft 9. This ensures the perpendicular alignment of the scalpel-like cutting edge (10) of the trocar (8), provided that the base section 1 is properly mounted.

A further variation of the invention provides that a blocking cannula 18 with two separate air channels be inserted into the passageway of the indwelling cannula. The one air channel 12 is equipped on the outside with a closure pad 13 and terminates on the inside in a closure sac 15. By pressing on the closure pad 13, this closure sac 15 can be blown up, as needed, inside the trachea above the point of the air supply line 16, thereby preventing an escape in the direction of the cranium of the air blown into the trachea 23 through this air supply line 16.

The indwelling cannula 5, which is straight and very short, gives the attending physician the additional possibility of visually inspecting, to an adequate degree, the trachea T, in which case, after removal of the trocar 8, a thin fiber-optic cable, also not represented in the figures, can be inserted additionally to illuminate the inner wall of the trachea. A suction device or the like can also be inserted through the indwelling cannula 5. Photographic recording is also possible by means of an endoscope introduced through the indwelling cannula 5. Finally, the fixative rim 6 can also be designed as a source of illumination of the trachea T. The use of such suction, illumination and/or visual inspection devices will be necessary for the attending physician only in occasional cases; however, the measures necessary to implement such devices can already be integrated into the coniotomy device at the time of production.

The coniotomy device is extremely easy to use, so that it can be administered without a problem by physicians, registered nurses or other assistants. In the case of intubation hindrances that make orotracheal intubation impossible, access into the trachea of the patient can be gained with the coniotomy device according to the invention. The procedure is the following:

The attending physician feels his way along the thyroid cartilage with his left index finger up to its lower border, so that the fingertip lies on the lig. conicum. The tip of the coniotomy device is placed on the skin of the hollow so created and pressed through the body surface perpendicularly into the tracheal region. Prior to insertion, the index finger is removed. At the same time, the thumb and middle finger hold the larynx of the patient in place. After inserting the scalpel-like cutting edge 10, slight resistance can be felt as it penetrates the elastic membrane, when the fixative rim 6 penetrates this membrane. At this moment, the tip of the trocar is still about 7 mm distant from the back wall of the trachea; consequently, there is only a minimal risk of injuring the back wall of the trachea. After removing the trocar 8, the physician can begin immediately with the artificial respiration of the patient by using an air-pump squeeze-pouch 7 or a so-called ambulatory bag or the like.

Naturally, the invention is not limited to the application in the closed breathing tract in the pharyngeal region and the nose, ears and throat area. In addition, the instrument can be used successfully in various other surgical applications.

What is claimed is:

1. A coniotomy device for artificial respiration with a trocar conducted through a cannula insertable into a patient's trachea and with a collar positioned externally on such a patient's neck for fastening the base section of the device to such a patient's neck, as well as an air-pump squeeze-pouch connected to the cannula, wherein the base section (1) has lateral fixative wings (2, 3) at its front, neck-side end and a connection piece (4) for an air-pump squeeze-pouch (7) at its back end and a short straight cannula (5), with a fixative rim (6) at its end, positioned centrally and projecting forwards in the direction of such a patient's neck, the cannula (5) is designed across its entire length as a passageway for the shaft (9) of a trocar (8), the shaft of which (9) being provided with a scalpel-like cutting edge (10); the base section (1), with its cannula (5), can be positioned perpendicularly to such a patient's neck and the cannula (5) can be introduced also perpendicularly into such a patient's trachea (23), the scalpel-like cutting edge (10) running from the cranial to the caudal direction and therefore parallel to elastic fibers of such a patient's ligamentum conicum.

2. The coniotomy device according to claim 1, wherein the length (L) of the section of the cannula (5) introduced into such a patient's body is about 17 mm, the inner diameter of the cannula (5) about 4–6 mm and its fixative rim (6) has a thickness of about 1 mm.

3. The coniotomy device according to claim 1, wherein a blocking cannula (18) can be inserted through the cannula (5) into such a patient's trachea (23) and a closure sac (15) for such a patient's trachea (23) can be blown up through its air channel (12).

4. The coniotomy device according to claim 3, wherein the cannula (5), the trocar (8) and the blocking cannula (18) have a fixative tongue and groove device (14).

5. The coniotomy device according to claim 3, wherein the blocking cannula (18) has an air channel (12) and a separate air supply line (16), the air channel (12) is closed on its outer side by means of a closure pad (13) and terminates in a closure sac (15) at its internal end.

6. The coniotomy device according to claim 1, wherein the cutting edge (10) of the trocar (8) is perpendicular to such a patient's cricoid cartilage (20) and does not protrude more than 7 mm beyond the fixative rim (6).

7. The coniotomy device according to claim 1, wherein the shaft (9) of the trocar (8) has a limit stop (11).

8. The coniotomy device according to claim 7, wherein the limit stop (11) can be varied.

9. The coniotomy device according to claim 1, wherein suction, visual inspection and illumination elements for such a patient's trachea (23) that can be inserted into the cannula are provided.

* * * * *